(12) United States Patent  
Orofino

(10) Patent No.: US 11,806,435 B2
(45) Date of Patent: Nov. 7, 2023

(54) SYSTEM FOR ADMINISTERING AND HEATING LIQUIDS

(71) Applicant: OROFINO PHARMACEUTICALS GROUP SRL, Rome (IT)

(72) Inventor: Ernesto Orofino, Rome (IT)

(73) Assignee: OROFINO PHARMACEUTICALS GROUP SRL, Rome (IT)

( * ) Notice: Subject to any disclaimer, the term of this patent is extended or adjusted under 35 U.S.C. 154(b) by 359 days.

(21) Appl. No.: 17/058,016

(22) PCT Filed: May 23, 2019

(86) PCT No.: PCT/IB2019/054269
§ 371 (c)(1),
(2) Date: Nov. 23, 2020

(87) PCT Pub. No.: WO2019/224762
PCT Pub. Date: Nov. 28, 2019

(65) Prior Publication Data
US 2021/0322275 A1 Oct. 21, 2021

(30) Foreign Application Priority Data
May 24, 2018 (IT) .................. 102018000005651

(51) Int. Cl.
*A61L 2/18* (2006.01)
*A61J 9/00* (2006.01)
(Continued)

(52) U.S. Cl.
CPC .................. *A61L 2/18* (2013.01); *A23L 2/00* (2013.01); *A61J 9/001* (2013.01); *A61J 9/006* (2013.01);
(Continued)

(58) Field of Classification Search
CPC ..... A61L 2/18; A23L 2/00; A61J 9/006; A61J 9/04; A61J 9/08; A61J 11/0005; A61J 11/04
See application file for complete search history.

(56) References Cited

U.S. PATENT DOCUMENTS

| 1,887,280 A | 11/1932 | Biancalana |
| 2,204,683 A | 6/1940 | Lambert |

(Continued)

FOREIGN PATENT DOCUMENTS

| WO | 0054818 A1 | 9/2000 |
| WO | 2004054414 A1 | 7/2004 |
| WO | 2007058441 A1 | 5/2007 |

OTHER PUBLICATIONS

International Search Report and Written Opinion for International Patent Application No. PCT/IB2019/054269, dated Oct. 22, 2019, 15 pages.

(Continued)

*Primary Examiner* — Sean E Conley
(74) *Attorney, Agent, or Firm* — Armstrong Teasdale LLP

(57) ABSTRACT

A device for heating and concomitantly administering a liquid includes a body having at opposite ends a base and a neck connectable to liquid suction means, and liquid heating means. The body has an inner housing configured to receive and completely enclose a liquid container. The inner housing has fluidic connection means. The neck has one or more tubes adapted to fluidically connect the fluidic connection means to the liquid suction means. The liquid heating means are adapted to heat at least partially the one or more tubes, and the fluidic connection means have one or more sharp spouts for puncturing of a predetermined region of the liquid container and for fluidic connection to the liquid container. A liquid container and a sanitizing system of the device are also provided.

5 Claims, 13 Drawing Sheets

(51) Int. Cl.
*A61J 9/04* (2006.01)
*A61J 9/08* (2006.01)
*A61J 11/00* (2006.01)
*A61J 11/04* (2006.01)
*A23L 2/00* (2006.01)

(52) U.S. Cl.
CPC . *A61J 9/04* (2013.01); *A61J 9/08* (2013.01); *A61J 11/0005* (2013.01); *A61J 11/008* (2013.01); *A61J 11/009* (2013.01); *A61J 11/0035* (2013.01); *A61J 11/04* (2013.01); *A61J 2200/42* (2013.01); *A61J 2200/72* (2013.01)

(56) References Cited

U.S. PATENT DOCUMENTS

| | | | |
|---|---|---|---|
| 5,354,274 A * | 10/1994 | Demeter | A61J 11/00 215/11.1 |
| 5,397,031 A | 3/1995 | Jensen | |
| 2006/0081599 A1* | 4/2006 | Anderson | A47J 36/2433 219/438 |
| 2006/0263237 A1 | 11/2006 | Holley, Jr. | |
| 2011/0151069 A1 | 6/2011 | Harding | |

OTHER PUBLICATIONS

International Preliminary Report on Patentability for International Patent Application No. PCT/IB2019/054269, dated Sep. 3, 2020, 49 pages.

\* cited by examiner

SYSTEM FOR ADMINISTERING AND HEATING LIQUIDS

CROSS-REFERENCE TO RELATED APPLICATIONS

This application is a National Stage Application of International Patent Application No. PCT/IB2019/054269, having an International Filing Date of May 23, 2019, which claims the benefit of priority to Italian Patent Application No. 102018000005651, filed May 24, 2018, the entire contents of which are hereby incorporated by reference herein.

FIELD OF THE INVENTION

The present invention relates to the field of systems for regulating the temperature of a liquid adapted for oral administration, as well as to that of systems for the oral administration of liquids.

BACKGROUND OF THE INVENTION

It is known that feeding bottles have not undergone any outstanding typological or technological evolution over the past decades, but an almost exclusively aesthetic or shape evolution.

Different families of feeding bottles are currently on the market, which differ mainly for place of use and method of use, notwithstanding the lack of technological innovation.

In particular, even within the same family, feeding bottles differ in the choice of materials, in the choice of color and in the choice of design, notwithstanding the original shape of the teat kept in almost all cases.

It is also known that, during administration, feeding bottles are subjected to different liquid temperatures, which change mainly according to the characteristics of the receiving subject to whom the liquid is administered, in particular age and psychophysical conditions of the receiver.

Such temperatures are currently managed by devices which are outside the feeding bottle and transmit the heat corresponding to the desired temperature, substantially by transferring it to the liquid at hand.

In particular, such liquid heating types are used by means of heated plates or by immersing the feeding bottle into a corresponding liquid at the desired temperature.

It is also known that the liquids are introduced manually and dosed upon insertion into the feeding bottle.

These methods are impractical and do not allow to regulate the temperature in a satisfactory and accurate manner.

Patent document U.S. Pat. No. 5,397,031 describes a device for heating the water to be introduced into a feeding bottle. It includes a housing for supporting a water bottle in inverted position and a heater for heating a predetermined amount of water. A flexible pipe is present for the interconnection between the feeding bottle and the heater, and a dosing valve is inserted between the feeding bottle and the heater, allowing the preselected amount of water to enter into the heater. A sensor is arranged inside a flexible pipe upstream of the dosing valve for detecting the water temperature which enters into the dosing valve itself. A control system, which is reactive to a manual switch for setting said predetermined amount of water, is supplied for actuating the heater for a sufficient time to heat said predetermined amount of water at a desired temperature. Liquid suction means are not provided because the liquid is poured into the feeding bottle in which the milk powder is also introduced. Therefore, the detected water temperature is not the final temperature of the administered milk, which is created in the feeding bottle and administered only later. Moreover, the feeding bottle must be opened before connecting it to the device according to the invention, and it is possible to connect it only with the opening upwards, in order not to spill part of the water. Therefore, the device of patent document U.S. Pat. No. 5,397,031 is not a heated feeding bottle and does not appear sufficiently sterile, not being truly any different from heated water in a kettle and then introduced into the feeding bottle.

A heated feeding bottle is known from WO 2004/054414, where heating means are inserted into a standard feeding bottle between the teat and the container body. Again, in this case, there are problems of sterility, because the body of the feeding bottle must be filled with milk and then the heater module and finally the suction means must be coupled. It must also be disassembled into three parts which are individually sanitized before further use, making it very impractical as well as non-sterile.

SUMMARY OF THE INVENTION

It is the object of the present invention to provide a system for administering and concomitantly heating liquids, inter alia, by way of example only, breast milk or reconstituted milk powder, which solves the problems and overcomes the drawbacks of the prior art.

It is the specific object of the present invention to provide a system of the aforesaid type, which allows to regulate, in particular, the actual administration temperature of a liquid, so as to allow the user (e.g. the caregiver of an infant) to regulate the temperature of the liquid according to the needs, as well as in relation to the age and the psychophysical needs of the receiver.

It is a further specific object of the present invention to provide a system for administering and concomitantly heating liquids which is practical, manageable and/or hygienic and/or sterile and/or easy to be sanitized.

The present invention relates to a device for heating and concomitantly administering liquid according to the appended claims.

The present invention further specifically relates to a liquid container (preferably pre-packaged) configured and adapted to be used with the device according to the invention, as defined in the appended claims.

The present invention further specifically relates to a method for heating and concomitantly administering a liquid which uses the device and the container according to the invention, as defined by the appended claims.

BRIEF DESCRIPTION OF THE DRAWINGS

The invention will now be described by way of example, with particular reference to the figures of the accompanying drawings, in which.

DETAILED DESCRIPTION

Figure 1:
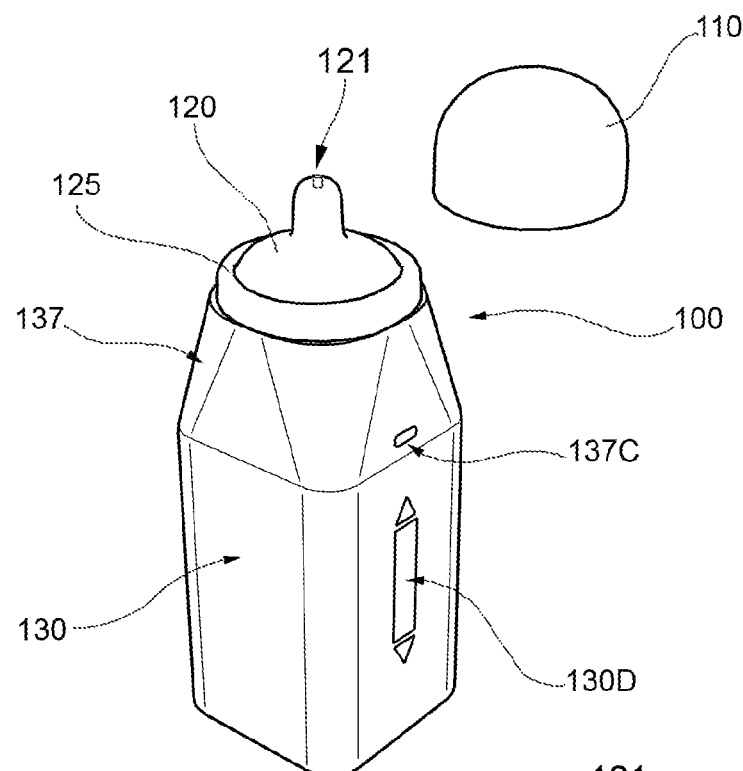
FIG. 1 shows a perspective view of the system according to the present description, with a separate cap and the body open.

It is worth noting that hereinafter elements of different embodiments may be combined together to provide further embodiments without restrictions with respect to the technical concept of the invention, as those skilled in the art will effortlessly understand from the description.

The present description also makes reference to the prior art for the implementation thereof, with regard to the detail features which are not described, such as, for example, elements of minor importance usually used in the prior art in solutions of the same type.

When an element is introduced, it is always understood that there may be "at least one" or "one or more". Furthermore, the term element must also be understood in general as "means" implementing the function of the element.

When a list of elements or features is recited in this description, it is understood that the invention according to the invention "comprises" or alternatively "consists of" such elements.

EMBODIMENTS

The system according to the present description comprises a device with a power source or which can be connected to a power source capable of providing heat to a liquid to be administered. In particular, the power source is an accumulator of electricity integrated in the device.

Hereinafter, the features of the profile of such a device will not be described in detail, because the technical effect ignores such details, and those skilled in the art can adapt them to the specific application case.

Hereafter, reference will be made to a feeding bottle, but it is apparent that the technical solution of the present description can also be applied to different devices for administering liquids, thus the term "feeding bottle" is here understood as a "liquid administering device".

Referring now to FIGS. 1-10, the feeding bottle 100 comprises a body 130, optionally a teat 120 and a cap 110 for the teat 120.

The teat 120, in turn, comprises a base ring 125 and a perforated tip 121. The base ring 125 also acts as a flange with the mouth 137B of the upper part 137 of the body 130, e.g. in a watertight manner, so that the liquid to be administered can exit only from the perforated tip 121.

Figure 2:
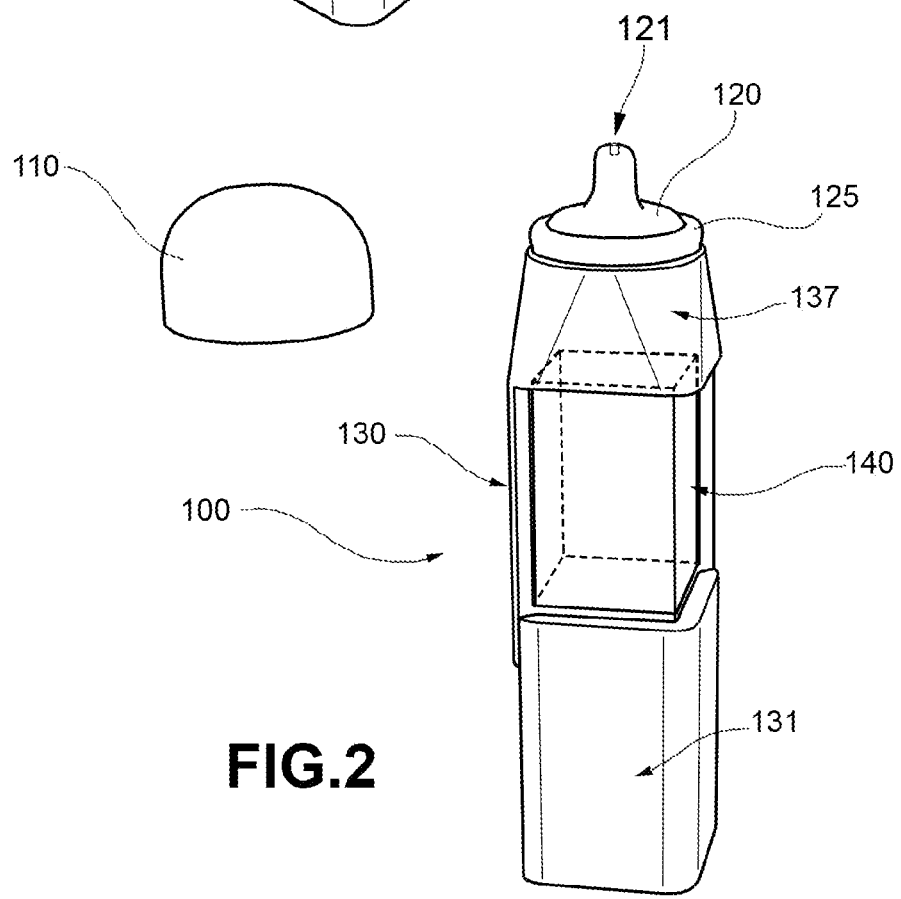
FIG. 2 shows a perspective view of the system according to the present description, with a separate cap and the body open, into which a liquid container is inserted.

As can be clearly seen in FIG. 2, the body of the device includes a further container 140, preferably independent. It can be introduced, for example, by firstly sliding a portion 131 of the outer wall of the body 130 to create an adequate (and predetermined opening) (alternatively the portion 131 can also rotate on a hinge). Hereafter, such a container will be conventionally referred to as a "cartridge" 140, thus being an exemplary case example of a disposable container prefilled with liquid. However, the invention can also use other generic containers.

Figure 3:
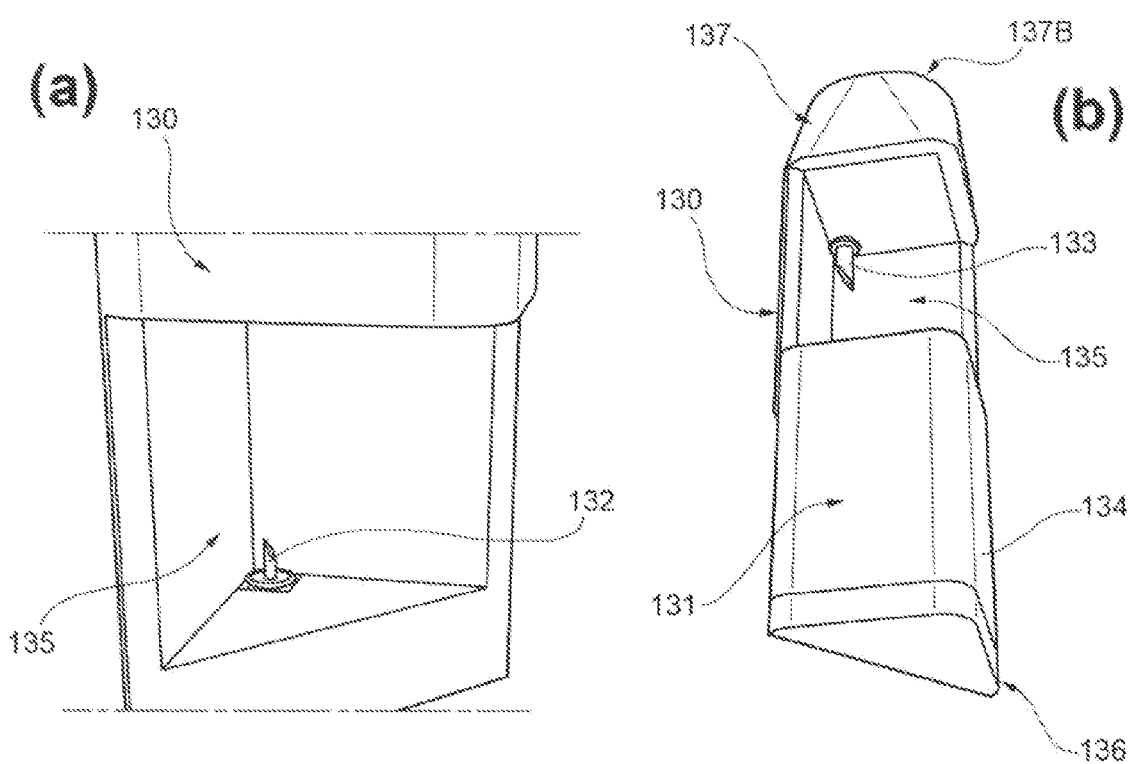
FIG. 3 shows a perspective view of a portion of the system according to the present description, with the open body and without the liquid container.

In FIG. 3, the opening created by sliding a portion of the wall can be seen, having omitted this portion of wall. It is worth noting that the housing 135 inside the body 130, in which a first spout 132, preferably sharp, which connects to the cartridge 140 is preferably arranged. FIG. 3(b) also shows the lower part 136 of the container 134, where 'low/high' means a position with respect to the force of gravity in relation to a device 100 in which the base 136 is on the horizontal (perpendicular to the force of gravity). It is worth noting in the same figure also a second spout 133, preferably sharp, on an opposite side to the first spout 132, in particular in front on the same vertical line, on the opposite wall of the housing 135 (the walls are preferably substantially perpendicular to the force of gravity in the case of parallelepiped housing).

Figure 4:
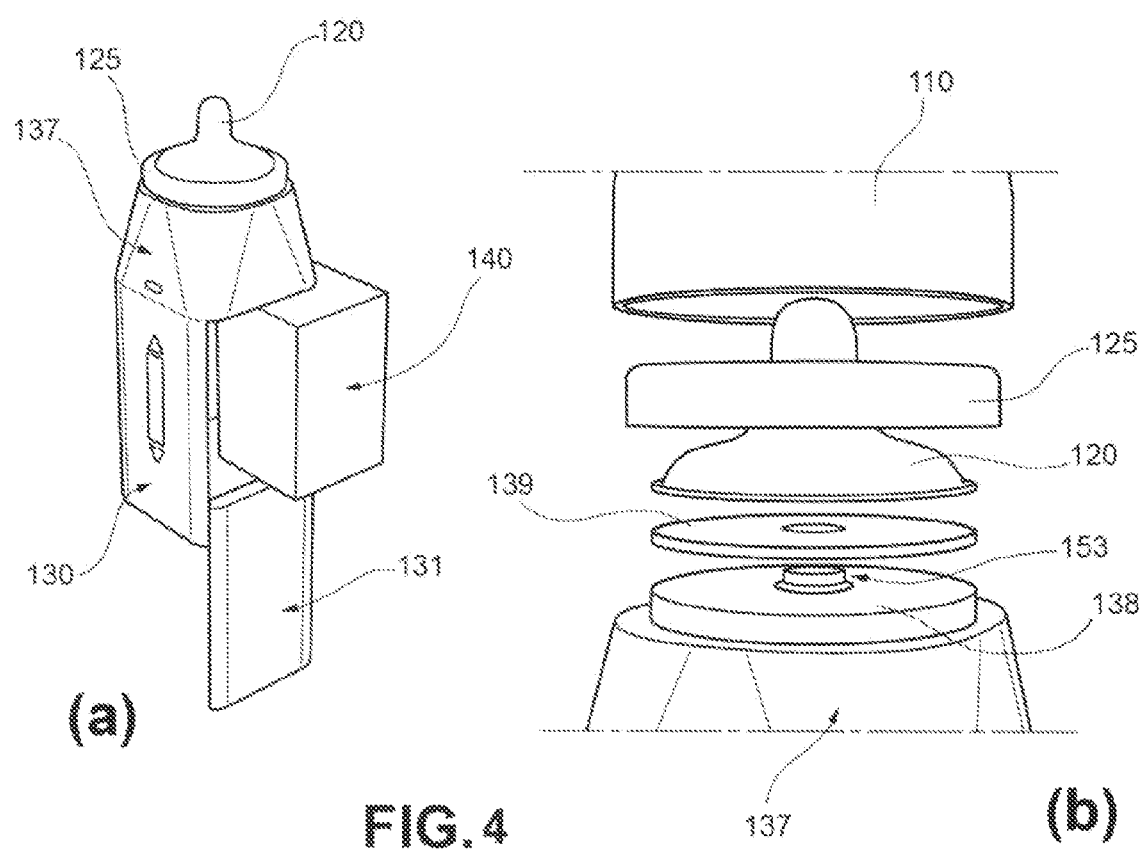
FIG. 4 shows in (a) a perspective view of the system according to the present description, with the body open and the liquid container inserted, and (b) a detail of (a) in which the teat is removed.

FIG. 4 shows in (a) the insertion of the cartridge 140 into the body 130, once the wall portion 131 has been moved, while in (b) it shows the detail of the upper part, exploded with respect to the teat 120. It can be seen that the disc 138 is a protrusion of the upper end surface 137B of the flared portion 137, and a sealing disc 139 which optionally surrounds the spout or liquid inlet valve 153 into the teat 120. The disc 139 allows a better tightness of the teat 120-upper part 137 connection of the body 130.

Figure 5:
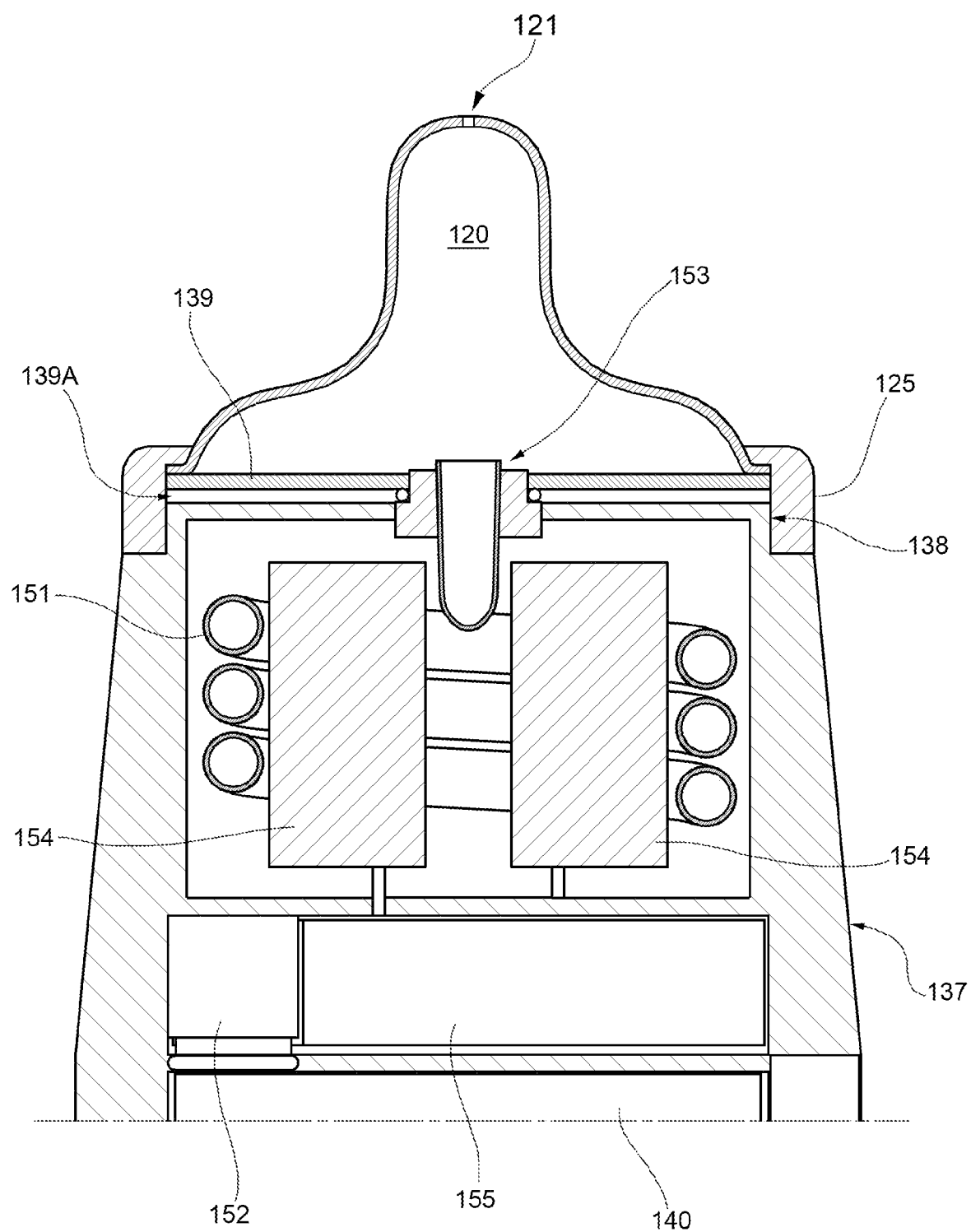
FIG. 5 shows a section view of a portion of the device in FIG. 2.

In this regard, the arrangement of the sealing disc 139 is shown in greater detail in FIG. 5. A seal 153G can be seen which spaces the sealing disc 139 from the disc 138, forming an air ring 139A between the two. Everything is held in place by the flange 125.

Figure 6:
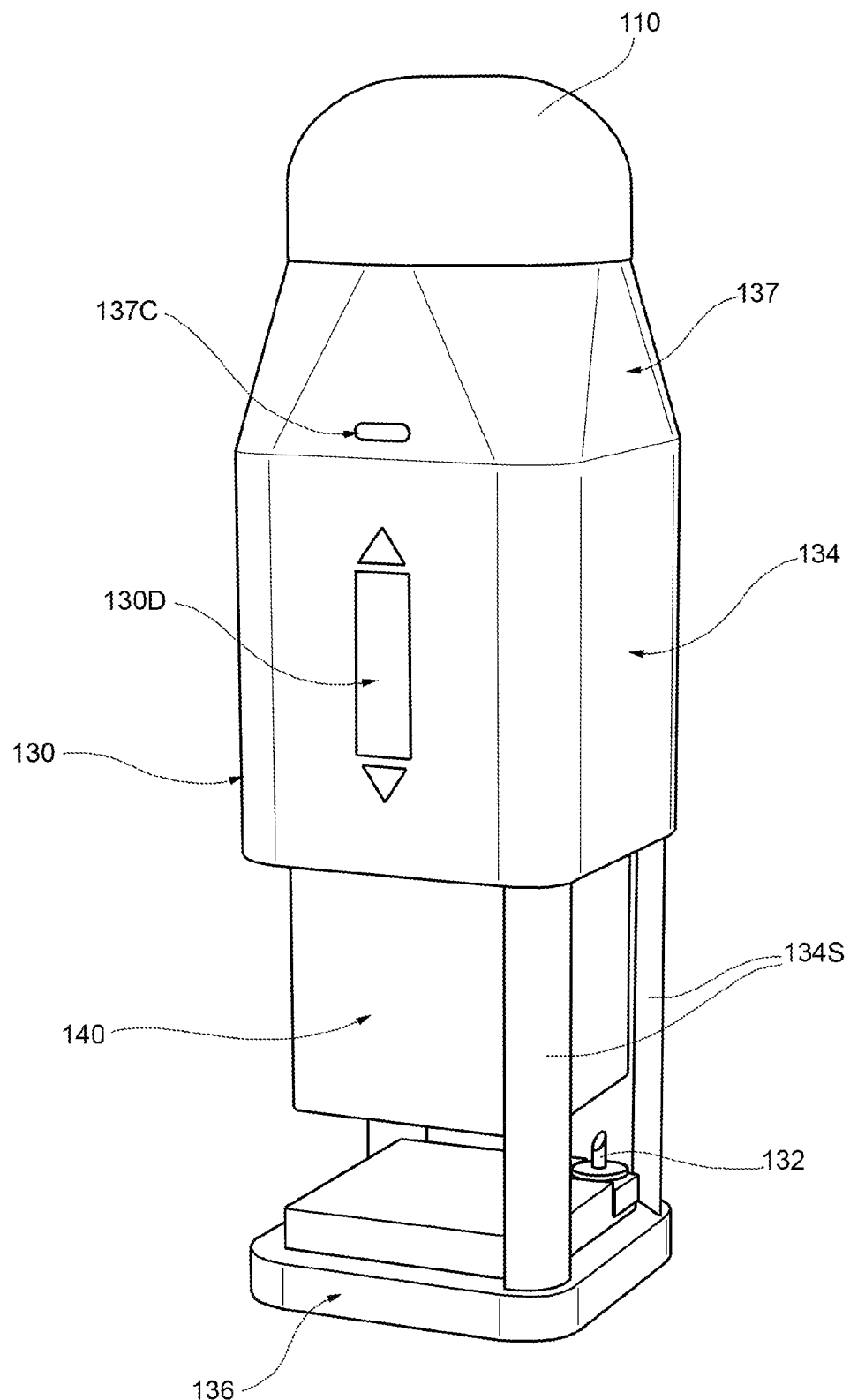
FIG. 6 shows a perspective view of the entire device in an aspect of the present description, in which the cartridge is loaded from below.

FIG. 6 shows a variant of the device according to the present description, in which the cartridge is loaded from below. In this case, for example, it is possible to slide the base 136 along integrated guides 134S so as to open the insertion space of the cartridge 140 and then close the base 136 itself so that the spout 132 punctures the cartridge itself (a seal may be present at the base of each spout described above, in order to prevent the spillage of liquid) or alternatively that other fluidic connection means are operational in connection with the cartridge 140.

Figure 7:
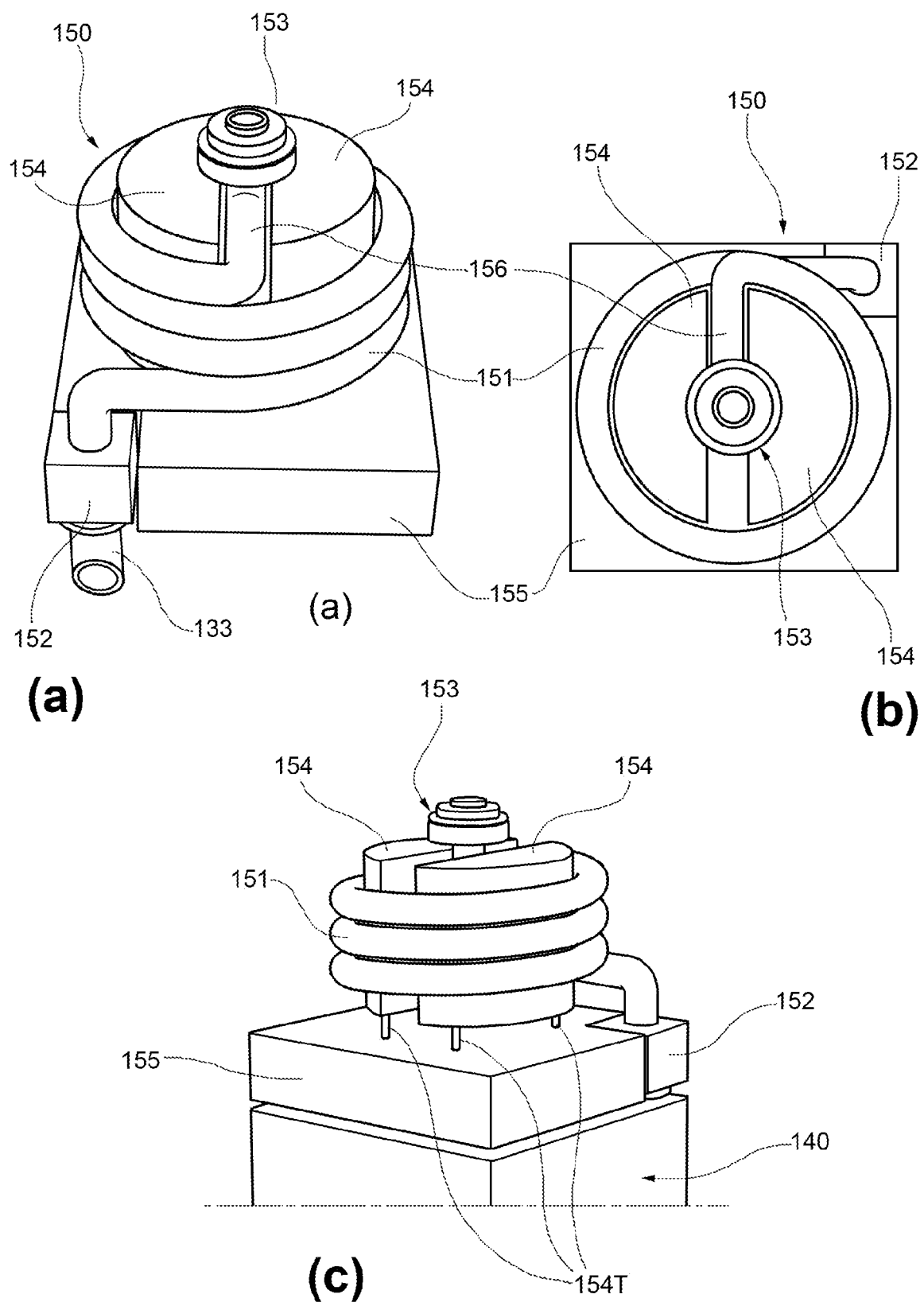
FIG. 7 shows in (a) a perspective view of the inner liquid heating system, in (b) a top view of the same system, and in (c) a further perspective detail view, according to the present description.
Figure 8:
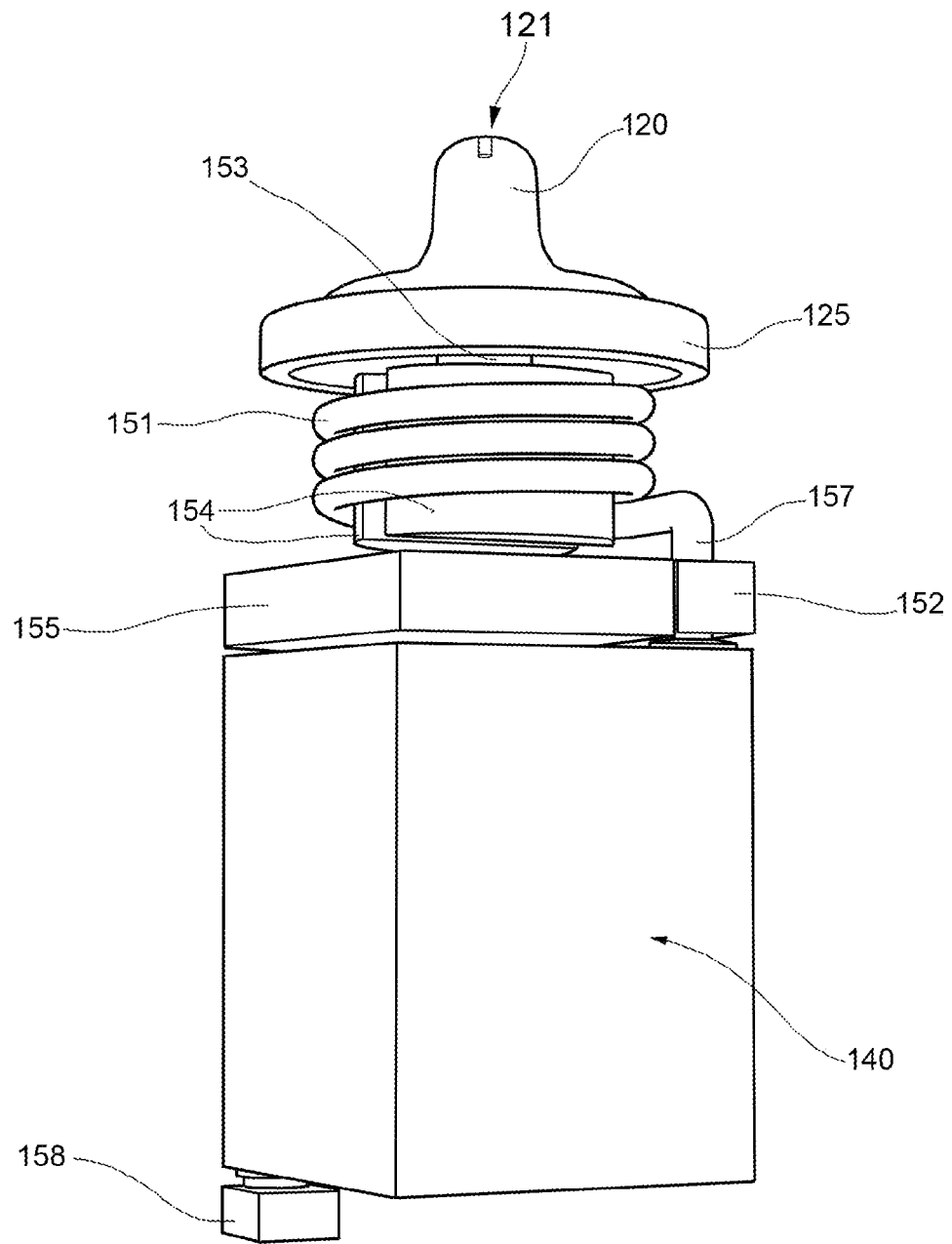
FIG. 8 shows a perspective view of the heating system in FIG. 7 connected to the liquid container on one part and to the teat on the other.

Referring to FIGS. 7 and 8, the heating system of the feeding bottle according to the present description comprises one or more tubes 151 which connect to the spout 133 and extend into the upper part 137 of the body 130.

The resistors could also be in the form of spiral which surrounds the part 151 (a tube with a spiral/resistor wound on it), or part 151 may be at the same time both the tube for the passage of the liquid or material adapted to be a resistor (therefore elements 154 and 151 can be united or integrated).

It could be hypothesized that the inserted heating means may be also or only inside the walls of the body 130, and thus would heat the housing 135 and then the cartridge 140. Thereby, the moment when the liquid is heated is anticipated and the effort by the resistors 154 would be less.

In an aspect of the present description, there is a tube 151 which connects to a further portion of tube 157 to the spout 133 and is wound in a serpentine and then connects to a further portion (e.g. linear) 156 to the spout or inlet valve 153. The tube 151 is optionally wound about two central resistors 154 and crosses them with the portion 156 to connect to the spout/channel/element or inlet valve 153. In a different embodiment, the resistors may be additionally or alternatively provided outside the serpentine 151. It is further worth noting that the resistors are connected to the accumulator in block 155 through contacts 154T. It is also possible to have only one resistor or two or more than two outside and/or inside the serpentine either in total or partial contact therewith or not.

Optionally, the serpentine winding is separated from the housing 135 and/or from the cartridge 140 by an accumulator housing block 155. If the accumulator housing block 155 is present, the tube 151 can cross it in a portion 152 thereof (preferably forming a corner of the block) to reach the spout 133. The block 155 may advantageously also contain electronics to regulate the temperature of the heating resistor. For this purpose, one or more thermocouples or equivalent temperature measuring device may be present in the chamber (not shown) which is formed between the teat 120 and the disc 139. This chamber may also act as a pre-heated liquid reservoir to ensure a continuous supply. Temperature sensors may also or alternatively be placed in close proximity to or in contact with the serpentine.

The electronics, according to the detected temperature and possibly an initial calibration, regulates the action of the resistors. It is also possible to provide a display 130D on the outer surface of the body 130 for displaying the temperature of the liquid to be administered, as well as possibly an on/off button of the device, which can be replaced or integrated with a remote activation system/management. For this function, it is possible to provide the insertion of a wireless connection device/system, potentially integrated in 155, e.g. identifiable in a Bluetooth connection. Furthermore, according to the present description, said remote activation means allow to remotely set the characteristics of the system, in particular the temperature to which the liquid must be taken. A USB port 137C or the like may also be present to charge the battery of the device.

Figure 9:
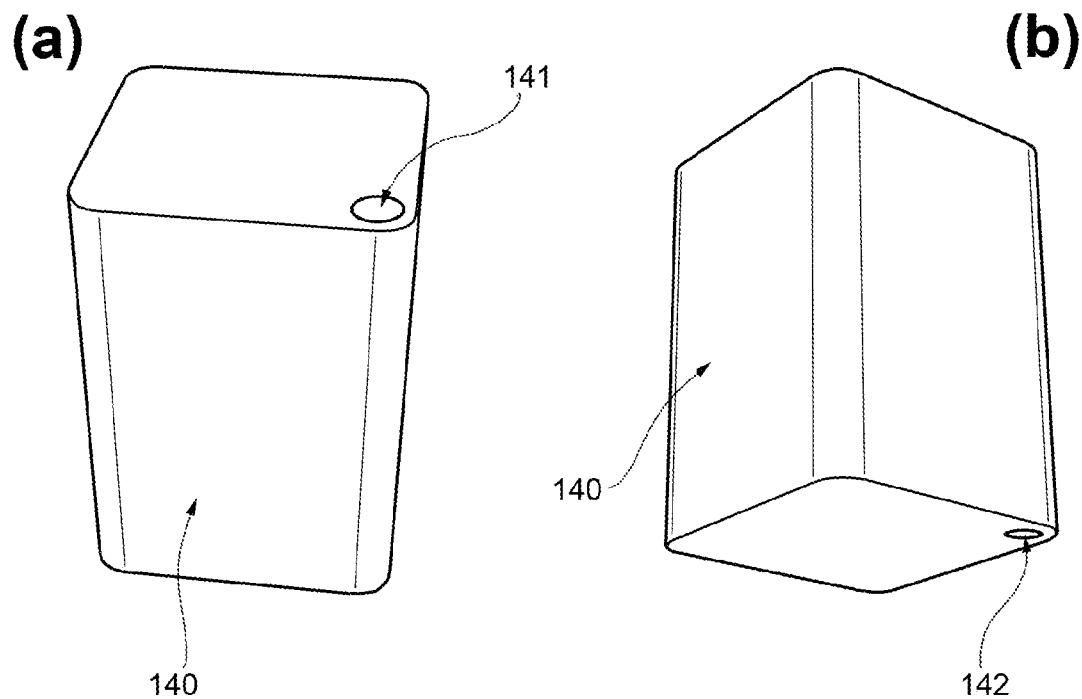
FIG. 9 shows two perspective views, from the top in (a) and from the bottom in (b), of the liquid container according to an aspect of the present description.

Turning now back to the cartridge 140, and referring to FIG. 9, this may have areas of lesser thickness 141, 142 (in general, any number and position) or different composition so as to be punctured by the spouts 132 and 133, after insertion into the housing 135. Conveniently, the puncturing occurs under the thrust of the wall portion 131 when it is closed, preferably when the cartridge is inserted from the bottom and closed by the base 136, as shown in FIG. 6. In an aspect of the present description, the cartridge 140 is a Tetrapak® and the puncturable zones 141, 142 do not have cardboard lining of the Tetrapak®.

Alternatively, there may be other fluidic connection means instead of the spouts 132, 133 and puncturable zones 140, 141 of the cartridge 140. This is particularly convenient when the cartridge 140 enters laterally and not from the bottom.

Figure 10:
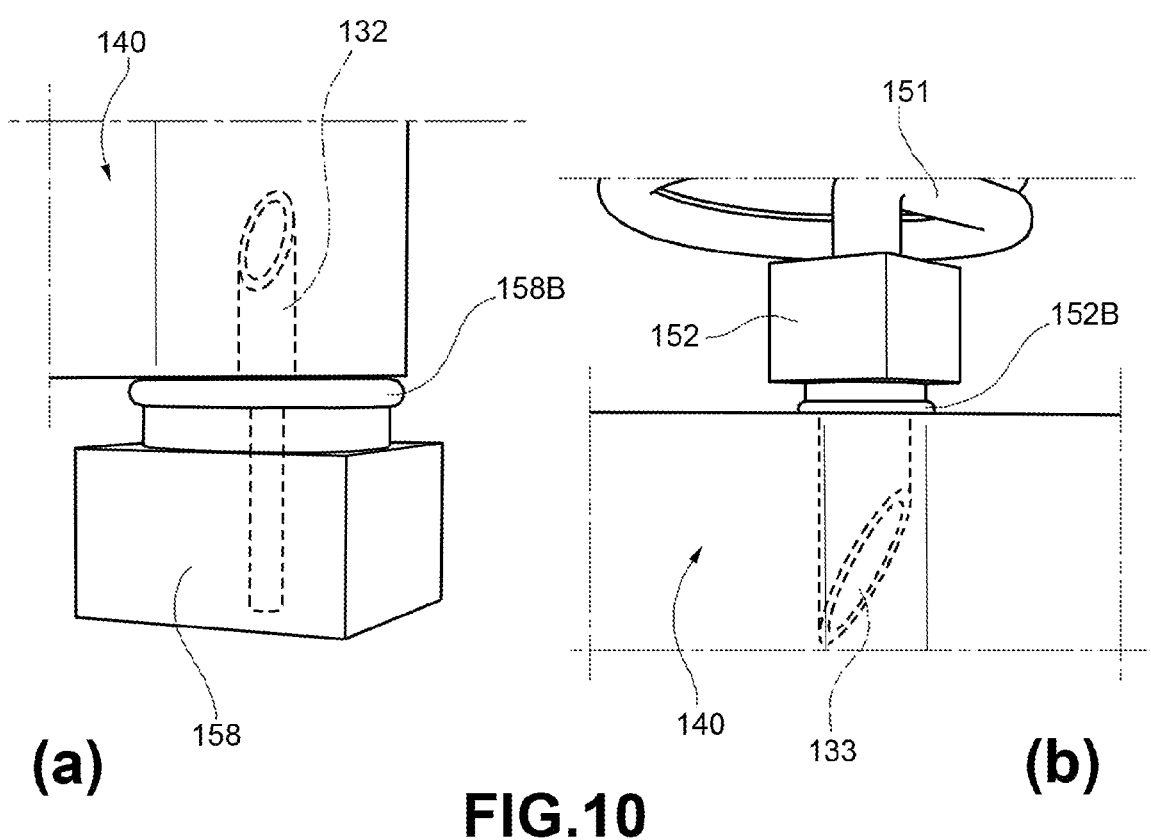
FIG. 10 shows the connection of the liquid container at the bottom of the body in (a) and at the top of the body in (b), according to an aspect of the present description.
Figure 11:
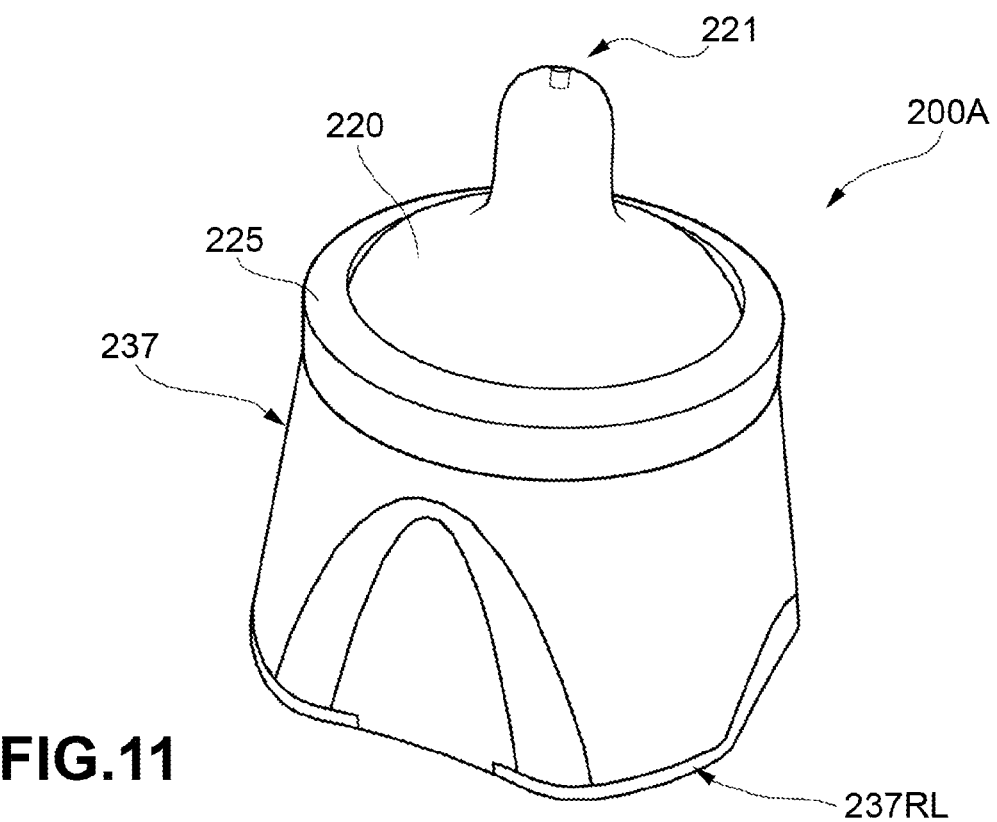
FIG. 11 shows a perspective view of the neck of a device according to the present invention.
Figure 12:
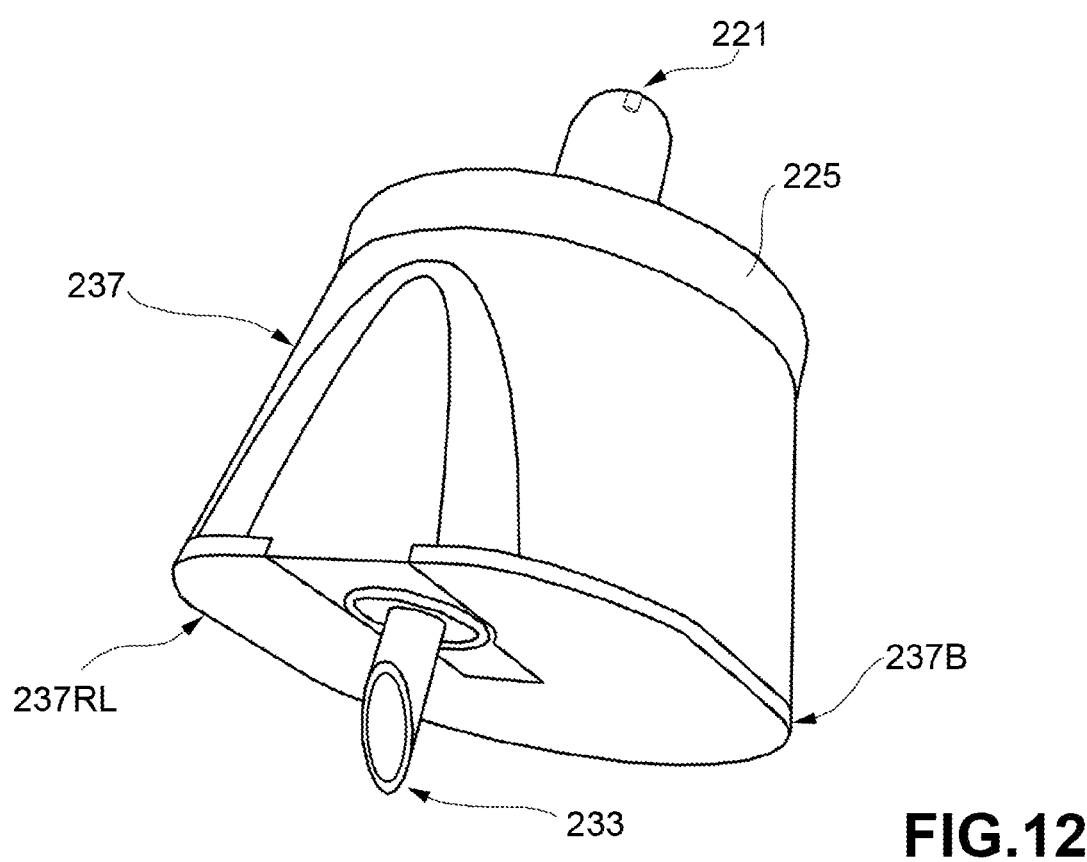
FIG. 12 shows a different perspective view of the neck in FIG. 11.
Figure 13:
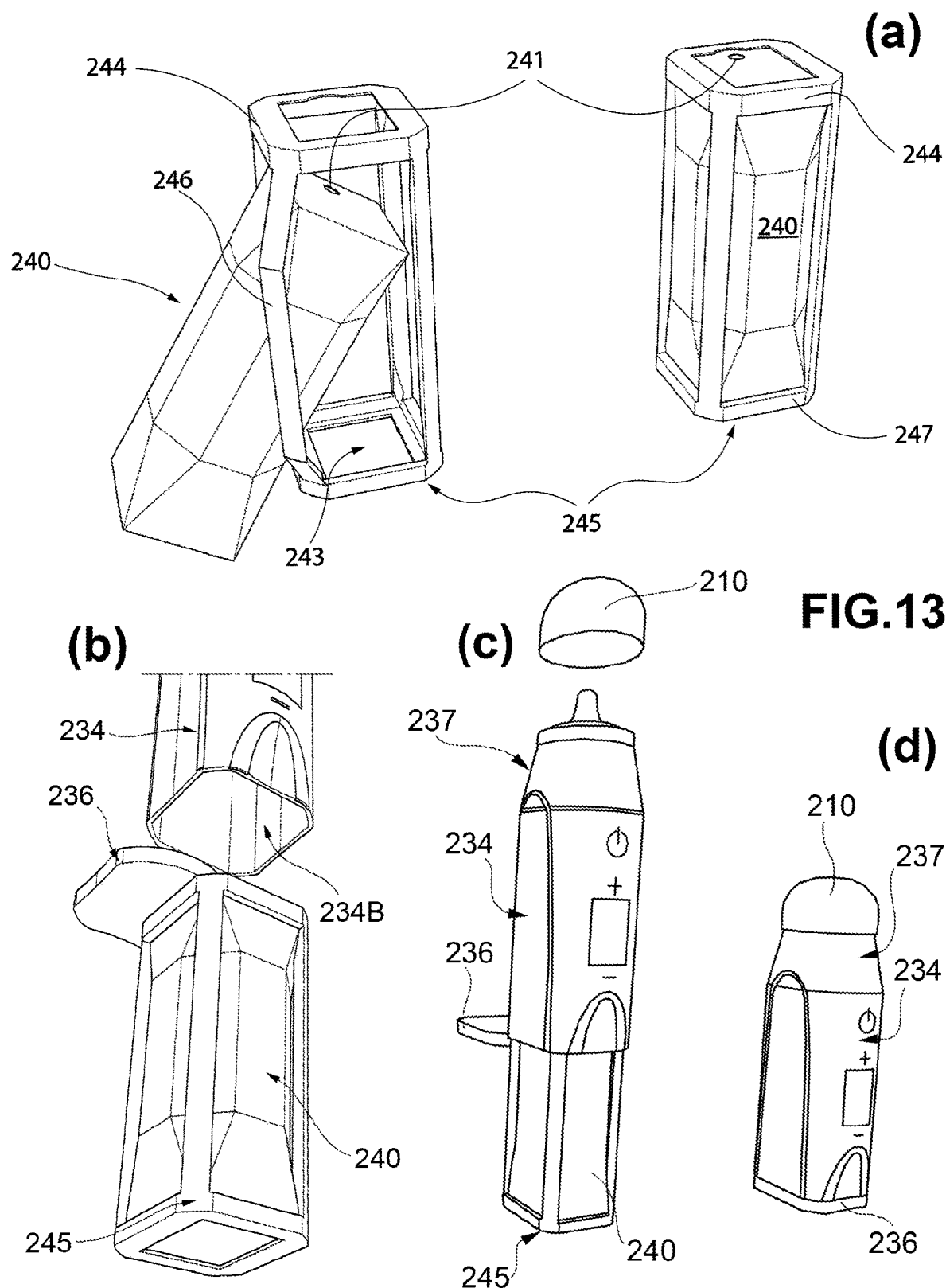
FIG. 13 shows in (a) a sequence of two perspective views of an exoskeleton which can be used in the device according to the invention, showing the insertion of the container into the exoskeleton itself; the figure also shows in (b) an insertion view of such an exoskeleton with the container filled, and in (c) a view of the device fully loaded and ready to use.
Figure 14:
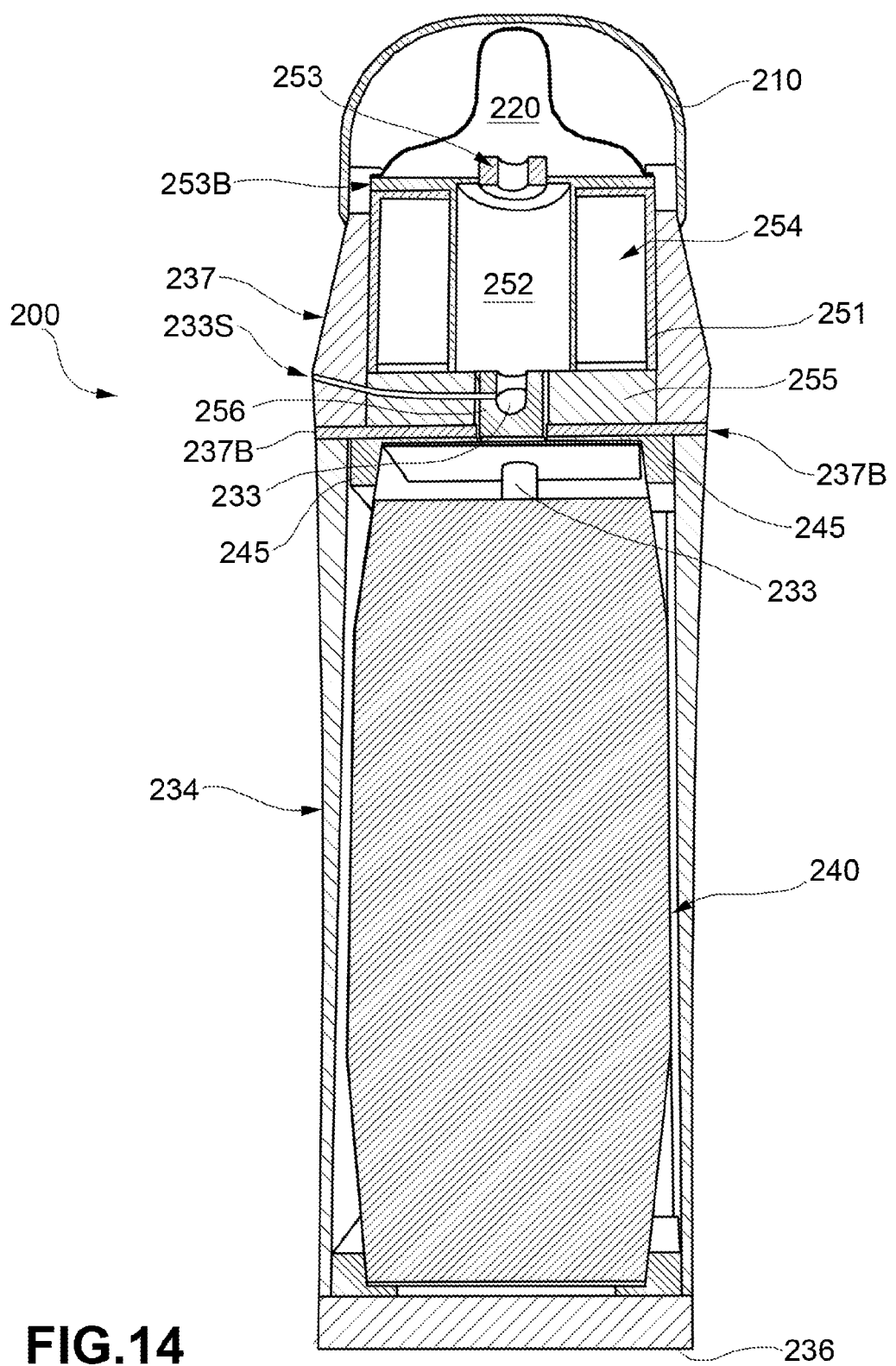
FIG. 14 shows a vertical section of the device in the configuration in FIG. 13(c)
Figure 16:
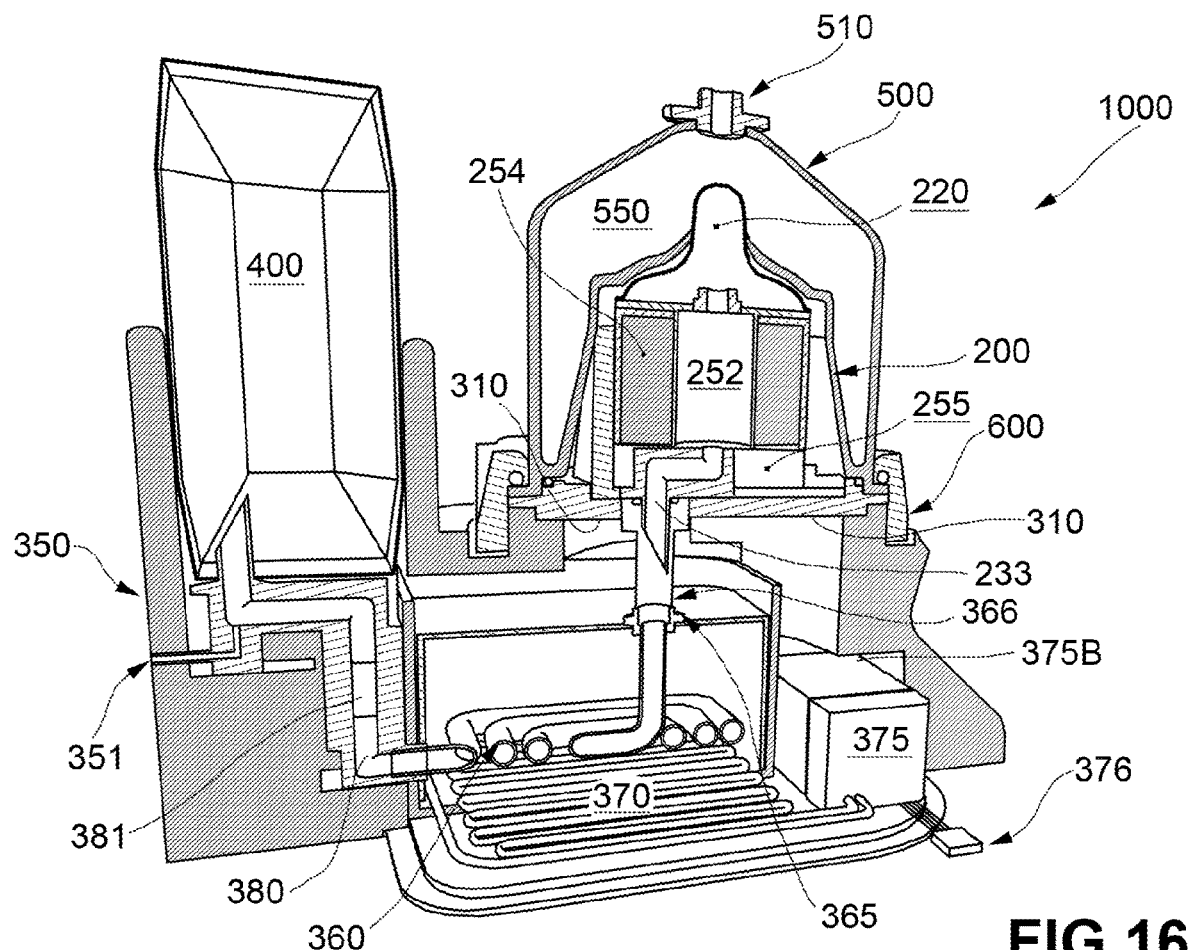
FIG. 16 shows a vertical section of the system in FIG. 15.
Figure 15:
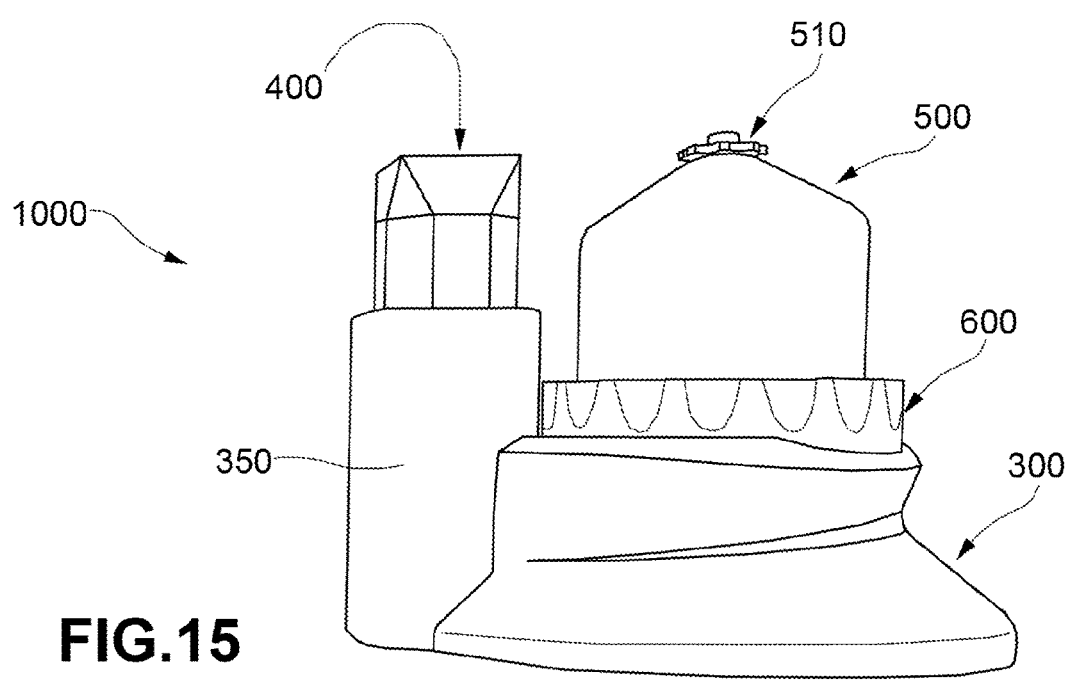
FIG. 15 shows an external view of the sterilization system according to the invention.
Figure 17:
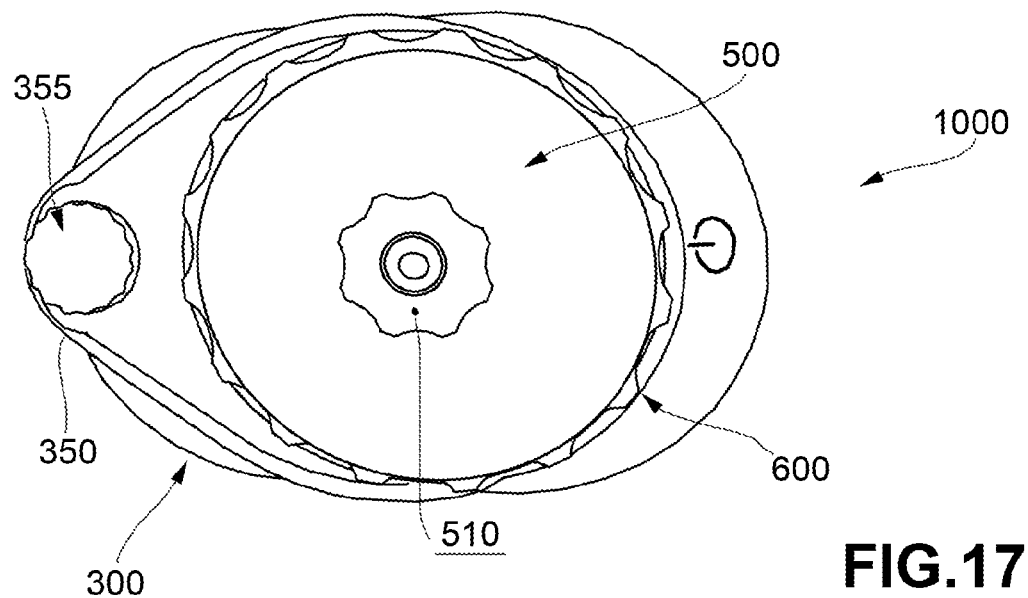
FIG. 17 shows a top view of the system in FIG. 15.
Figure 18:
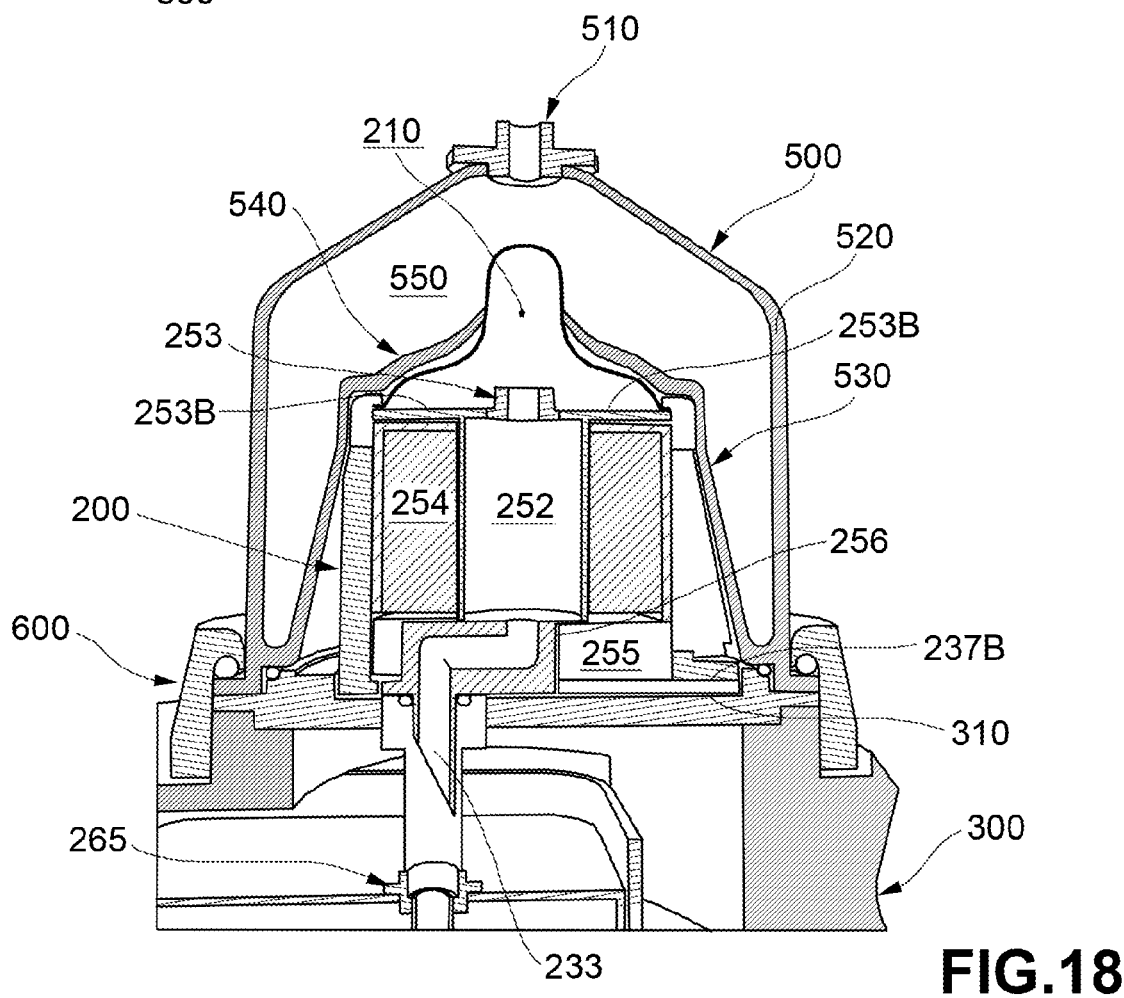
FIG. 18 shows a detail view of the section in FIG. 16.

In connection with the spouts 132 and 133, there may be respective connecting elements or valves 158, 152 to regulate the flow of liquid to be administered and provide an air inlet, also for the purpose of regulating the flow, so as to provide a path for the liquid to be administered and an air intake to allow the liquid to flow. The air inlet can be made in any other equivalent way. FIG. 10 shows respective seals 158B and 152B to prevent leakage of liquid. In a different embodiment, the spout 133 or other fluidic connection means can be found at the bottom of the housing 135, because it comes into action when the feeding bottle 100 is rotated horizontally.

In a different embodiment, the spout 132 and the respective air inlet means may be positioned on the upper part of the housing 135 for the sake of simplicity and manufacturing feasibility of the object 100, more specifically of the part 130.

A further embodiment will be disclosed now with reference to figures from 11 to 20.

The illustrated device 200 is a device for heating and concomitantly administering a liquid, as in the previous embodiment. As can be seen, it may include:
- a body 234, which includes in turn at opposite ends:
  - a base 236, and
  - a neck 237, which can be connected to suction (administration) means 220 of the liquid;
- heating means 254 of the liquid, e.g. powered by a battery included in said body 234.

In an advantageous manner, the device is such that:
- the body 234 comprises an inner housing 234B configured and adapted to receive and enclose a liquid container 240, preferably pre-packaged (e.g. completely, but may have open parts, the important aspect is that the container is held in place);
- the inner housing 234B comprises means 233 for the fluidic connection with said liquid container; and
- the neck 237 comprises one or more tubes 252 (only one in the figure) adapted to fluidically connect said fluidic connection means 233 to said suction means 220.

Reference numeral 245 also indicates instead the frame in which the container 240 is placed before being inserted into the body of the device.

Reference numeral 237B indicates the base of the neck 237.

Figure 19:
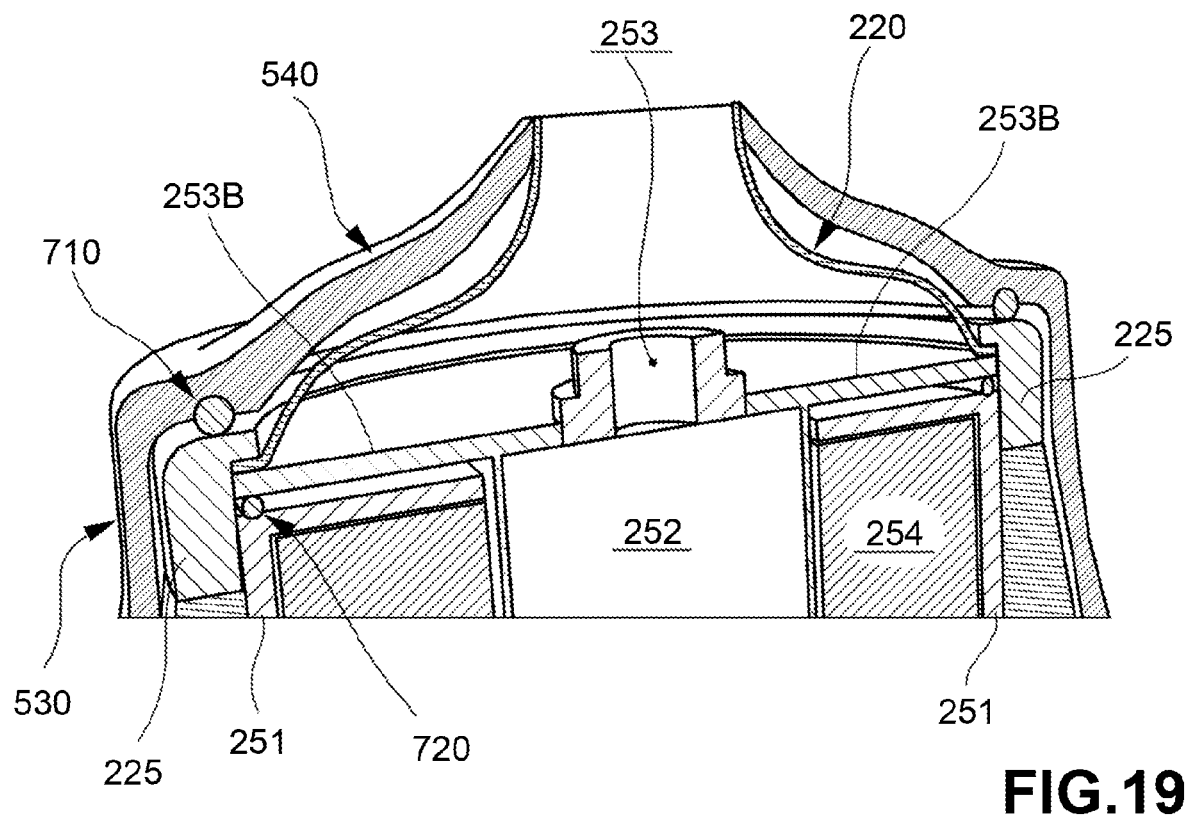
FIG. 19 shows a further detail view of the configuration in FIG. 16.

In the device according to an aspect of the invention, the heating means 254 are adapted to heat said one or more tubes 252 at least partially. Outside the heating means, there may be insulating means 251, as shown in FIG. 19. The same figure shows also optionally a division disc 253B between the compartment of the teat 220 and duct 252.

According to an aspect of the invention, the fluidic connection means 233 comprise one or more sharp spouts for puncturing a predefined region 241 for fluidically connecting to said pre-packaged liquid container 240.

An aspect of the invention comprises at least a first temperature sensor configured and adapted to detect a temperature of at least one portion of said one or more tubes 252.

The suction means 220 (e.g. including an infant teat), when connected, may form a chamber 220 between them and said neck 237, the chamber being configured to receive said liquid, at least a second temperature sensor configured and adapted to detect a temperature of the liquid and/or of said chamber being present in said chamber.

A control logic may be present, being adapted to detect the temperature of said first and/or second temperature sensor and regulate the activation of said heating means 254. For example, the control logic may be configured and adapted to send temperature information to a user signaling device which is integrated on said body 234 and/or wirelessly connected to said control logic.

According to an aspect of the invention, the inner housing 243 can be at least partially closed by closing means 236, e.g. by a sliding wall. The closing means 236 may be configured to push, in use, the liquid container 240 against said one or more spouts sharp 233 until it is punctured.

Preferably, there is a single spout 233 rigidly connected or integrated into the base of the neck 237.

The inner housing comprises, according to a further aspect of the invention, a removable frame 245 configured to receive said pre-packaged liquid container 240. The removable frame allows to compensate for the dimensional tolerances of each cartridge, thus allowing to insert it with greater ease.

The sharp spout 233 may be fluidically connected to the outside of the device through a vent duct 233S.

Neck-body connection means may be provided according to the available technique, e.g. by means of snap-on connection.

This all applies also to the first embodiment, although here the tube 252 is different and the heating means 254 have different shape, and moreover the second sharp spout is no longer necessary.

The container 240 may comprise one or more container fluidic connection means 241 configured and adapted to connect to said fluidic connection means 233, respectively. According to an aspect of the invention, the fluidic connection means 241 for the container comprise a container wall portion which can be punctured by said sharp spout 233. This wall portion may be protected against contaminants by a peelable element (not shown), to be removed before inserting the container into the device of the invention.

The container may be a Tetrapak®, in which for example the puncturable wall portions 241 do not have the cardboard lining of the Tetrapak®.

The method for heating and concomitantly administering the liquid are the same as in the embodiment in FIGS. 1 to 10.

Associated with the heating and administering device according to any one of the embodiments shown by way of example in the figures, according to the invention, there may be a sanitizing device 1000 for sanitizing the device 100;200 for heating and concomitantly administering a liquid. The sanitizing device may comprise:
- a base 300 with:
  - a portion 350 for at least partially inserting a sanitizing liquid container 400;
  - a connection opening with the neck 137;237 of the liquid administering device 100 as described and claimed herein;
  - a protective dome 500 of said neck 137;237;
  - a connecting flange 600 between said base 300, said neck 137;237 and said dome 500;
  - one or more fluidic connection ducts 380,360,366 between said sanitizing liquid container 400 and said neck 137;237; and
  - liquid heating means 270 at least partially along said one or more fluidic connection ducts. 380,360,233.

Additionally, there may be a portion or part 310 of the base 300, configured and adapted to support/accommodate the section 237 to be sanitized.

The sanitizing device 1000 may be such that the dome 500 has a first wall 520 and a second wall 530 connected to and inside the first wall, forming a gap 550 therebetween. Advantageously, the second wall 530 has an opening through which a portion of the perforated tip 121;221 of suction means 120;220 emerges in use. In this case, the gap 550 can be a gap closed between the perforated tip, the first wall 520 and the second wall 530. Furthermore, the dome 500 may include a vent valve 510 on the first wall 520.

The sanitizing device 1000 advantageously comprises the portion 350 for at least partially inserting a sanitizing liquid container 400, which has an opening for inserting said sanitizing liquid container 400 opposite to a supporting base for the device 1000.

Advantageously, the sanitizing device 1000 is such that the one or more fluidic connection ducts 380,360,366 comprise one or more end connection portions 366 adapted to receive respectively an end portion of said one or more spouts, so as to form a gap 367 therewith for the sanitizing the outer surface of said one or more spouts. Thereby, not only the pipes through which the liquid to be administered will be sterilized, but also the outer walls of the spout, which together with the peelable element, makes the system according to the invention totally sterile.

The sanitizing liquid container 400 may be loose, i.e. may be a container which can be refilled and not a pre-packaged container as shown.

Therefore, in practice, either after or before using the administration device according to the invention, the neck will be uncoupled and it will be coupled by means of the appropriate flange 600, to the base 300, covering it at the same time with the dome 500 which will be secured with the same flange. A sanitizing refill 400 will be placed in the housing 350 and the automatic device 1000 will be will actuated. The liquid in 400 will descend along the pipes 380 also due to the action of an in-line pump 381. This will be possible also by virtue of a vent 351 which connects to the pipe 380, e.g. between the refill 400 and the pump 381.

From the pipes 380, the liquid will pass to the serpentine 360 which is thermally coupled with a heating serpentine 370, powered by a power supply or battery 375B which can be connected to the electric network by means of electrical contacts 376. Reference numeral 375 indicates chipset for managing the entire system and for managing the battery (e.g. comprises wireless connection means of NFC/Bluetooth type or the like). Naturally, the chipset can also be placed elsewhere in the device 300.

Figure 20:
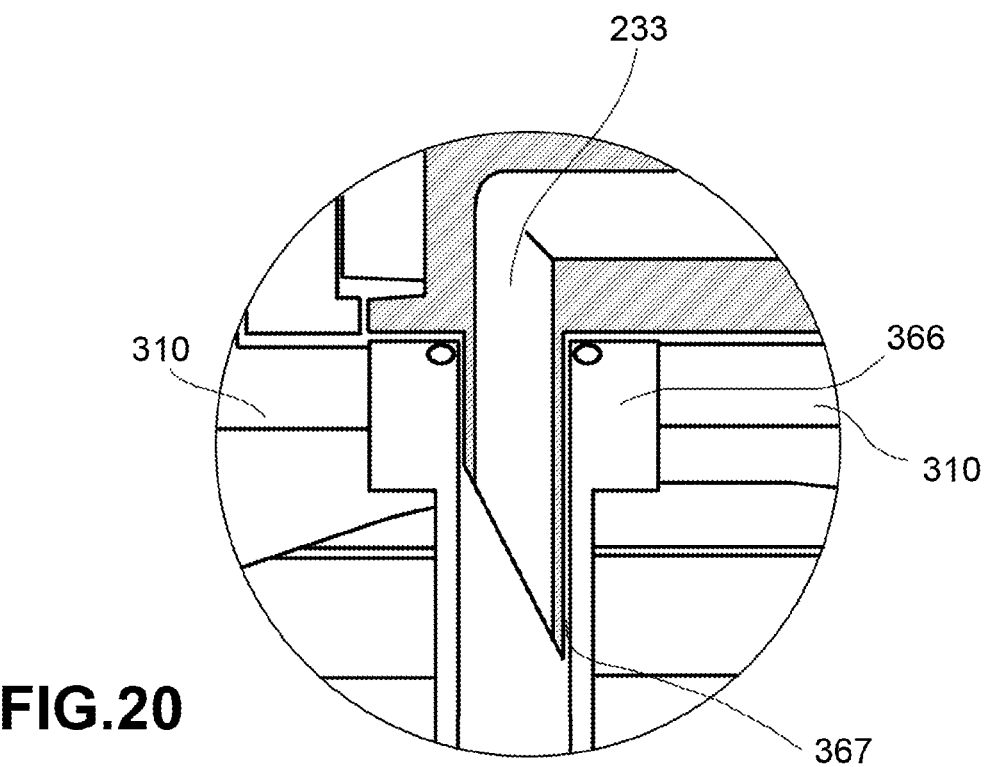
FIG. 20 is a particular detail view of the view in FIG. 19.

The serpentine 360 will end vertically with a valve 365 which connects to a pipe 366 which receives the spout 233, connection shown in greater detail in FIG. 20, in which it can be seen that the sanitizing liquid enters both inside the spout 233 and outside it in 367, so as to sanitize it from both sides.

The figures also show a given number of seals for sealing the various parts, where needed. For example, seals 710 and 720 in FIG. 19 allow to isolate the teat portion 210 which does not escape. In particular, seal 720 is a seal between the base 256, 253B and the insulating part 251 and the heating element 254. Those skilled in the art may conveniently arrange the required number and type of seals to ensure optimal operation of the apparatus as a whole.

ADVANTAGES OF THE INVENTION

The suggested solution according to the present invention solves the problem of managing dosage and of raising the temperature of the liquid, allowing the user to have a customized regulation of the thermal characteristics of the liquid in relation of the receiver (infant) and to simplify the moment of dosing by means of one or more pre-filled cartridges and then adapt them to the specific conditions and needs of the receiver and to the context of use in which the administrator operates.

The solution therefore allows the use of one or more pre-filled cartridges during the preparation step of the feeding bottle. Such cartridges may be sold separately from the rest of the system.

By virtue of the solution of the present description, it is possible to regulate the thermal characteristics of the feeding bottle remotely via device (smartphone or the like) and dedicated app.

With respect to the device of the document U.S. Pat. No. 5,397,031, the invention allows to integrate the water heater with the feeding bottle so that the whole is easy to handle and sterile. However, the document of the prior art describes separate elements for heating and administering, because the passage of pure water does not need sanitation, and the feeding bottle is instead sanitized separately in a traditional manner.

In addition, the prior art device does not have an internal housing configured to accommodate and surround (e.g. completely) a liquid container, presenting itself instead as a support for a water bottle in the inverted position. This makes the device difficult to handle, unlike the present invention. Even performing the connection in advance in a position with the feeding bottle resting on a support, it is still difficult to handle. With the device according to the invention, the container of liquid to be administered may be inserted in any position, because it is intended to be closed within the same device. This avoids any contamination and spillage during use.

Still, the water bottle is traditionally connected through its integrated opening, whereas in the invention the container has no openings until it is punctured by a sharp spout present inside the device. This obliges the user of the prior art to open the feeding bottle before connecting it to the heater, while in the invention the opening and the connection is simultaneous, whereby limiting or eliminating the exposure of the liquid to the elements of the surrounding environment. The puncturing of the present invention does not create the possibility of contamination because it occurs after having removed a protective tongue located in the puncturing region in the step of manufacturing of the container. The sanitizing of the sharp spout takes place by detaching the neck from the body of the feeding bottle and using, for example, the sanitizing device according to the invention. Finally, with the device according to the invention there is no need to prepare the milk before administration, heating it fully, but it is heated gradually as it is being administered, in order to save energy.

With respect to the device of document WO 2004/054414, the invention prevents the body of the feeding bottle from needing to be filled manually with milk from external source, and avoids the time needed to couple the body of the feeding bottle to the heater module and finally the latter to the suction means. Furthermore, the invention provides for the sterilization of the device before or after use, disassembly into two parts instead of three, and a dedicated, automatic sterilization system, thus making the present solution much more practical in addition to sterile.

LIST OF REFERENCES IN THE DRAWINGS

100=liquid administering device
110=teat cap or other administration means
120=teat or other administration means
125=flange for connecting the teat 120 to the neck 137 and to the surface of the element 138/139
130=body of the device 100
131=means for closing the housing 135, in particular a sliding door to totally or partially complete the walls of the body 130
132=lower pointed spout, or lower fluidic connection means
133=upper pointed spout, or upper fluidic connection means
134=body portion 130 between the base 136 and the housing 135
135=housing configured to receive the pre-packaged liquid container 140
136=base of the body 130
137=neck of the body 130, either tapered upwards or not
137B=free upper edge/surface of the neck 137
137C=USB socket or other type of connection for charging the device
138=projecting portion on the surface 137B
139=sealing element placed inside the edge 137B and to which the flange 125 connects or on which it rests
139A=gap, e.g. filled with air, formed between the sealing element 139 and the protruding portion 138
140=pre-packaged liquid container
141=zone of the container 140 which is free from cardboard (thinner or puncturable zone), on the upper base of the container (in each case, a first zone)
142=possible further zone of the container 140 which is free from cardboard (thinner or puncturable zone), preferably at the bottom of the container
150=heating and fluidic connection means between the pre-packaged liquid container 140 and the teat 120
151=vertical serpentine pipes
152=passage portion or element of the tube 151 and element/valve for managing the flow direction
152B=seal, e.g. annular
153=spout/channel/element or inlet valve 153, in general liquid outlet element or means
154=resistors or heating means
155=accumulator housing block and possibly of control electronics
156=connecting pipe portion between the vertical spiral tube 151 and the introduction valve/element 153
157=connecting pipe portion
158=air inlet element
158B=seal, e.g. annular
200=device for administering liquids
200A=upper portion or head of the liquid administering device
210=teat cap or other administration means
221=perforated tip of the teat cap
220=teat or other administration means
225=flange for connecting the teat 220 to the neck 237 and to the surface of the element 253B
233=upper pointed (sharp) spout or upper fluidic connection means, which also act as a sanitizing duct portion going from the serpentine 360 to the head 200A 234=casing of the lower portion (body) of the liquid administering device
234B=inner compartment 234 for inserting 240 and 245
236=base of the casing 234 and liquid administering device
237=upper portion or neck of the liquid administering device
237B=base of the upper portion 237
237RL=lower edge (closer to the casing 234) of the base 237B
240=container of liquid to be administered
241=puncturable portion of the container 240
243=empty central portion of the base 247
244=upper base of the frame 245 for inserting the container 240
245=frame for inserting the container 240
246=side for inserting the container 240 into the frame
247=lower base of the insertion frame 245
251=thermal insulation component between the heating system 254 and the rest of the upper section of the feeding bottle 237
252=flowing tube of the liquid being heated
253=valve for introducing the liquid into the teat 220
253B=separation disc between the compartment of the teat 220 and duct 252
254=means for heating the liquid surrounding the tube 252
255=compartment for housing the management system (chipset or the like/battery, etc.) for the heating system present in 237. However, the chipset may also be located elsewhere, e.g. in 234
256=valve for introducing the liquid from the container 240 to the upper portion 237
300=base of the device 1000
310=portion or part of 300, adapted to support/accommodate the section 237 to be sanitized
360=serpentine for flowing the sanitizing liquid in the base 1000
365=valve for introducing the sanitizing liquid from the serpentine 360 to the portion of sanitizing duct 233
370=heating serpentine facing the flowing serpentine 360 chipset for managing the entire system and
375=for managing the battery (comprises wireless connection means of NFC/Bluetooth type or the like)
375B=battery for powering the sanitizing device 1000
376=external electric socket contacts connected to the battery 375B
380=duct going from the sanitizing liquid container 400 to the flowing serpentine 360
381=portion of the base of the sanitizing device 1000 which houses the pump means
350=portion of the base of the sanitizing device which at least partially accommodates the sanitizing liquid container 400
351=vent duct connected to duct 380
400=sanitizing liquid container
500=dome for housing the upper portion 237 of the liquid administering device
510=vent valve of the dome 500
520=first wall of the dome 500
530=second wall of the dome 500, inside the first wall 520
540=upper portion of the second wall 530
550=empty portion between the outer wall 520 of the dome 500 and the inner wall 530 of the dome
600=flange for connecting the dome 500 to the base portion 300
710=seal of the teat 220 towards the inner wall 530 of the dome 500
720=seal between the base 253B and the insulating part 251 and the heating element 254
1000=sanitizing device Hereto, the preferred embodiments have been described and some variants of the present invention have been suggested, but it is understood that those skilled in the art can make modifications and changes without departing from the respective scope of protection, as defined by the appended claims.

The invention claimed is:

1. A kit for administering a liquid by an administering device and for sanitizing the administering device, the kit comprising:
an administering device for heating and concomitantly administering the liquid;
a sanitizing device for said administering device;
wherein the administering device comprises:
    a body comprising at opposite ends a base, and a neck connectable to liquid suction means;
    liquid heating means;
    said body comprising an inner housing configured and adapted to receive and completely enclose a pre-packaged liquid container;
    said inner housing comprising fluidic connection means for fluidic connection to said pre-packaged liquid container;
    said fluidic connection means comprising one or more sharp spouts for puncturing a predetermined region of and fluidic connection to said pre-packaged liquid container;
    said neck comprising one or more tubes adapted to fluidically connect said fluidic connection means to said liquid suction means;
    said liquid heating means being adapted to heat at least partially said one or more tubes;
    said administering device comprises at least one first temperature sensor configured and adapted to detect temperature of at least one portion of said one or more tubes;
    said liquid suction means, when connected, forming a chamber between said liquid suction means and said neck, the chamber being configured to receive said liquid;
    said administering device further comprises at least one second temperature sensor configured and adapted to detect temperature of the liquid present in said chamber and/or of said chamber; and
    said administering device further comprises a control logic adapted to detect temperature of said first and/or second temperature sensors and control activation of said liquid heating means;
and wherein the sanitizing device comprises:
    a base comprising:
        a portion configured for at least partially inserting a sanitizing liquid container from outside the base;
        an opening for connection only to the neck when connected to the liquid suction means and detached from the body of the liquid administering device;
    a protective dome for said neck and said liquid suction means;
    a connecting flange for connecting said base, said neck and said dome together;
    one or more fluidic connection ducts between said sanitizing liquid container and said neck; and
    liquid heating means at least partially along said one or more fluidic connection ducts;

wherein said one or more fluidic connection ducts comprise one or more end connection portions adapted to receive an end portion of said one or more sharp spouts, respectively, so as to form a gap therewith for sanitizing an outer surface of said one or more sharp spouts.

2. The kit of claim 1, wherein said dome has a first wall and a second wall connected to and inside the first wall, which form a gap therebetween.

3. The kit of claim 2, wherein said liquid suction means have a perforated tip and said second wall has an opening through which, in use, a portion of the perforated tip emerges, said gap being a gap enclosed between the perforated tip, the first wall and the second wall.

4. The kit of claim 1, wherein the portion for at least partially inserting a sanitizing liquid container has an insertion opening for inserting said sanitizing liquid container, the insertion opening being opposite to a supporting base of sanitizing the device.

5. The kit of claim 2, wherein the dome includes a vent valve on the first wall.

\* \* \* \* \*